United States Patent

Maes et al.

[11] Patent Number: 4,705,681
[45] Date of Patent: Nov. 10, 1987

[54] HAIR TREATING COMPOSITION

[75] Inventors: Daniel Maes, Monroe, Conn.; Norman Brudney, Paris, France

[73] Assignee: Richardson-Vicks Limited, Egham, England

[21] Appl. No.: 713,890

[22] Filed: Mar. 20, 1985

[30] Foreign Application Priority Data

Mar. 21, 1984 [EP] European Pat. Off. .......... 84103104

[51] Int. Cl.$^4$ .......................... A61K 7/06; A61K 7/42
[52] U.S. Cl. ............................... 424/70; 424/DIG. 4; 424/59
[58] Field of Search ..................... 424/70, 59

[56] References Cited

U.S. PATENT DOCUMENTS

| | | | |
|---|---|---|---|
| 3,109,777 | 11/1963 | Zviak | 424/DIG. 4 |
| 3,251,741 | 5/1966 | Fox | 424/71 |
| 3,322,635 | 5/1967 | Erlemann et al. | 424/DIG. 4 |
| 4,201,235 | 5/1980 | Ciavatta | 424/70 |
| 4,478,853 | 10/1984 | Chaussee | 424/59 |

FOREIGN PATENT DOCUMENTS

| | | | |
|---|---|---|---|
| 0035919 | 9/1981 | France | 424/70 |
| 1603639 | 11/1981 | United Kingdom | 424/70 |

OTHER PUBLICATIONS

American Perfumer & Cosmetics, 1970, vol. 85, No. 2, pp. 47-51; LaPorte.
Chemical Abstracts, vol. 59, p. 2588(a), Wlaker.
Martindale, Extra Pharmacopoeia, 24th edition, 1958, vol. I, p. 1394.
Chemical Abstracts, 1949, p. 4434f, Hoffman LaRoche.
Merck Index, 1976, 9th edition, pp. 909 & 386.
Chem. Abs., 1971, vol. 74, p. 95182a, Sheppard et al.
Chem.Abs., 1968, vol. 68, p. 11492s, Casadio et al.
Chem. Abs., 1965, vol. 62, p. 13052(a), Kohiga et al.

Primary Examiner—Dale R. Ore
Attorney, Agent, or Firm—Salvatore R. Conte

[57] ABSTRACT

An improved hair treating or conditioning composition that decreases the friction between hairs thereby facilitating in combing and brushing of hair treated therewith contains a formulation which is a mixture of d-panthenyl ethyl ether and d-panthenol in a weight ratio of about 9 parts d-panthenol ethyl ester to about 1 part d-panthenol. Such hair treating or conditioning compositions also exhibit decreased damaged to hair treated therewith due at least in part to a decrease or reduction in abrasion between hairs.

5 Claims, 1 Drawing Figure

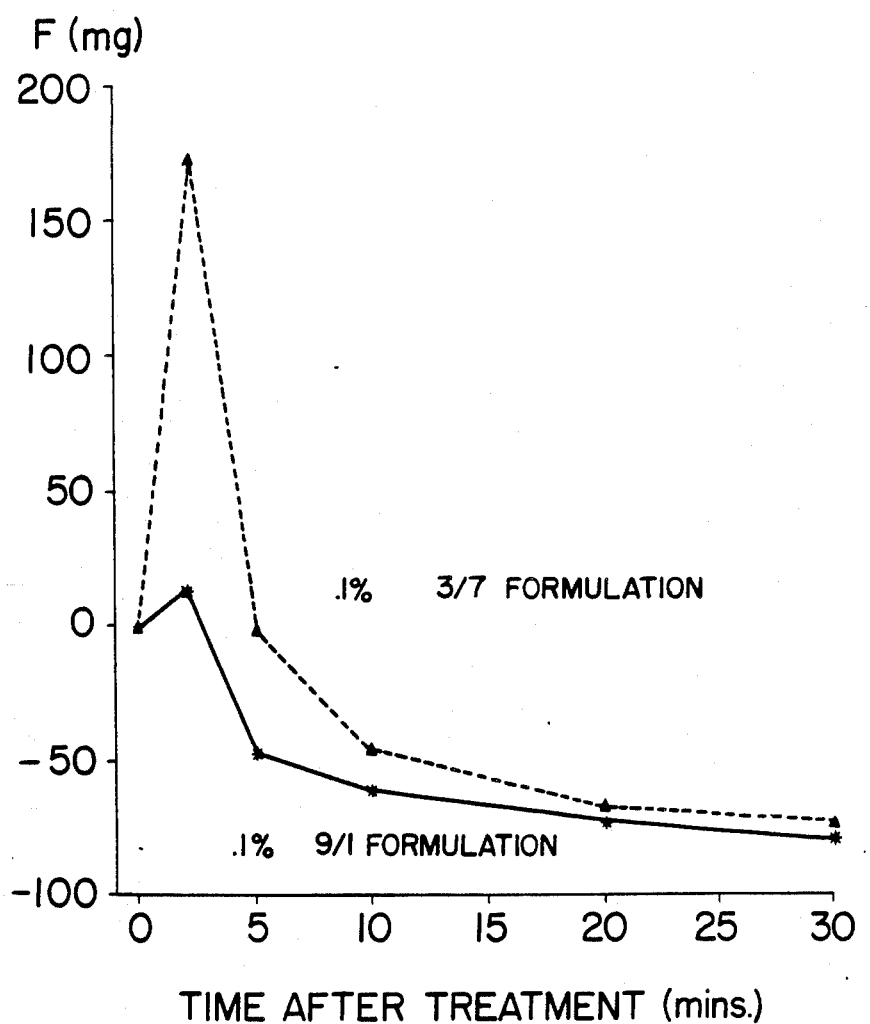

HAIR TREATING COMPOSITION

FIELD OF THE INVENTION

This invention relates to a new formulation for inclusion in hair treating or conditioning compositions and to the resulting hair treating or conditioning compositions containing such formulation.

BACKGROUND OF THE INVENTION

It has been recognized that after shampooing the hair it is desirable to utilize hair treating or conditioning compositions to improve the comb out and hair setting characteristics as well as to provide less entangling of the hair. Although a multitude of products have been suggested and marketed for such use, none have been without their drawbacks and disadvantages. Moreover, there is still a desire for products having improved comb out, hair setting and detangling characteristics.

Hair has also been found to be subject to abrasion damage caused by a multitude of factors such as grooming, combing, towelling and the like. Such hair abrasion is certainly one of the most severe damages a hair fiber is subjected to during its life cycle on the scalp. Such damage results in the removal of the protective cuticle layer and consequent exposure of the more fragile fibril/matrix complex arrangement of the cortex. Heretofore it has been the aim of a large number of capillary treatments to prevent or reduce such abrasion damage. This is generally attempted by coating the hair fiber with a polymeric substance designed to protect the hair against further damage. Users have not generally found such polymeric coating to be that desirable or effective.

It is therefore an object of this invention to provide an improved hair treating or conditioning composition that avoids or substantially lessens these drawbacks and disadvantages in previously employed products and/or which new compositions prevent or reduce abrasion damage to hair and which when used on hair provide improved comb out, hair setting and detangling due to a reduction in hair friction.

SUMMARY OF THE INVENTION

According to this invention a formulation of 9 parts by weight d-panthenyl ethyl ether and 1 part by weight d-panthenol when utilized in a hair conditioning or treating composition provides compositions which impart a decrease in friction between hairs resulting in less difficulty to comb and brush and also in less entangling of hairs. Such compositions allow for improvement in comb-out and hair setting. Additionally, such compositions also prevent or reduce abrasion damage between hairs.

DETAILED DESCRIPTION OF THE INVENTION

The formulation of 9 parts d-panthenyl ethyl ether and 1 part d-panthenol can be incorporated in hair conditioning or treating compositions in an amount generally of from about 0.05% by weight to about 10% by weight of the composition. Most preferably about 0.1% to 0.5% of the formulation is employed in the composition. It is surprising that hair care compositions containing the 9/1 formulation of this invention do not induce a large increase in friction immediately (within two minutes) and do decrease hair abrasion after treatment with such compositions since hair treated with a similar hair composition commercially available but containing 3 parts by weight d-panthenyl ethyl ether to every seven parts by weight d-panthenol exhibits both a significantly large increase in hair friction immediately after treatment and increases rather than decreases hair abrasion damage.

The formulation of this invention can be incorporated into any suitable hair conditioning or treating compositions of non washout product form such as lotions, creams, solutions, gels, sprays and the like, but preferably in lotion compositions. The hair composition can contain other ingredients normally or customarily found in such compositions such as antibacterial agents, emulsifiers, dye, colorants, perfumes and the like. Also, the formulation may be incorporated into hair washing preparations such as shampoos, hair and scalp conditioners and the like.

The novel formulation of this invention can be prepared by simply mixing 9 parts by weight d-panthenyl ethyl ether with one part by weight of d-panthenol. d-Panthenol is (R)-2,4-dihydroxy-N-(3-hydroxypropyl)-3,3-dimethylbutamide. Such formulations are then suitable for incorporation into any suitable hair care composition in an amount of from about 0.05% by weight to about 1% by weight, preferably about 0.1% to 0.5% by weight.

The unexpected absence of large increases in hair friction immediately after use and decrease in hair abrasion after use of the hair care composition of this invention is illustrated by the following comparative tests.

HAIR FRICTION TESTS

Hair samples were obtained from the same volunteer and washed with a commercially available shampoo. The hair samples were then treated with a commercially available hair composition containing 0.1% by weight of d-panthenyl ethyl ether and d-panthenol in a weight ratio of these two components of 3 to 7 and by a corresponding hair care composition of this invention of the identical composition except for the replacement of the 0.1% 3 to 7 ratio components with 0.1% by weight of the formulation of this invention, namely a formulation of 9 parts by weight d-panthenyl ethyl ether to 1 part by weight d-panthenol. The composition of these two hair care composition is set out in TABLE 1 hereinafter.

TABLE 1

| Components | Invention Composition Containing 0.1 9/1 Ratio w/v | Commercial Composition Containing 0.1 3/7 Ratio w/v |
|---|---|---|
| Absolute Ethyl alcohol | 35.00 v/v | 35.00 v/v |
| Antibacterial agent | 0.050 | 0.050 |
| Perfume | 0.100 | 0.100 |
| Non-ionic Emulsifier | | |
| d-Panthenyl ethyl ether | 0.09 | 0.03 |
| d-Panthenol | 0.01 | 0.07 |
| Ultraviolet filter agent | 0.025 | 0.025 |
| Colorant | 0.00062 | 0.00062 |
| Lactic acid q.s. pH | 5.5 | 5.5 |
| Deionised water q.s. | 100 ml | 100 ml |

The test apparatus and methodology consisted of a group of 4 hairs of the treated hair sample which is threaded perpendicularly through a hair bundle made up of about 40 hairs. The hair to hair friction was determined by measuring the force required to pull the group of 6 hairs through the tightly packed hair bundle using an electrodynamometer.

A maximum of 8 grams force was exerted by the electrodynamometer to pull the group of 6 hairs, whereas 6.5 grams weight was attached to the opposite end of the group of 6 hairs in order to bring them back to their original position upon release of the tension exerted by the electrodynamometer. During each measurement, the force generated by the electrodynamometer to pull the hair through the bundle increased linearly from 5 to 8 grams, at a rate of 6 mg per second, which induced a translation speed of 0.23 mm/second during the movement of the hairs across each other.

The hair care compositions were applied in a standardised manner by wiping each of the 6 hairs using a paper tissue soaked with the composition.

Each measurement which was carried out before and at standardised time intervals after treatment was repeated three times. Each experiment was carried out 5 times with the same hair care compositions using hair sample from the same donor.

The results of the hair friction measurements are shown in FIG. 1 and it will be noted that whereas the commercial composition containing 0.1% of the 3/7 formulation induced a large increase in hair friction at two minutes the composition containing 0.1% of the 9/1 formulation induced no large increase in hair friction at two minutes, and a substantial decrease in hair friction at five minutes onward, post treatment. Since combing or brushing of the hair generally occurs within five minutes of shampooing and conditioning of the hair, the composition of this invention permits much easier combing, brushing and hair setting and much less entangling of the hair.

HAIR ABRASION TEST

Hair samples were taken from the same switch in a hair bank and activated. Before conducting the abrasion test, a large hair switch was made radioactive after soaking 1 hour in a solution of $^{14}C$ labelled amino acids which composition is similar to the composition of keratin polypeptides.

The excess of solution was then blotted off and the hair samples allowed to dry at ambient conditions. The solution of amino acids employed for activation was the following:

| | |
|---|---|
| L - Alanine | 9.4% |
| L - Arginine | 7.0% |
| L - Aspartic acid | 10.0% |
| L - Flutamic acid | 9.0% |
| L - Glycine | 6.0% |
| L - Histidine | 1.5% |
| L - Isoleneine | 6.0% |
| L - Leucine | 12.5% |
| L - Lysine | 5.0% |
| L - Phenylalamine | 7.5% |
| L - Proline | 5.5% |
| L - Serine | 3.0% |
| L - Threonine | 5.5% |
| L - Thyrosine | 6.0% |
| L - Valine | 6.0% |

Treatment of the hair samples with hair care compositions was done by carefully wiping one half of the previously activated hair switch with a piece of absorbent paper soaked with the composition. The other half of the radioactive hair switch was used as a control and remained untreated.

Two hair care composition treated and two untreated hair switches (about 16 cm in length) were wrapped around a rotating cylinder which had been previously covered with non radioactive hair fibers, using double sided adhesive tape. The contact between the hair samples and the rotating cylinder was achieved by hanging a 9 gram lead weight on the free end of each hair sample, the other end being maintained in a fixed position by a clamp. The abrasion was achieved on 7 cm along the hair by rotating the cylinder at 780 rpm in order to induce a significant friction in a direction against the scales of the hair.

After being abraded, each hair sample was cut in 2 cm length segments from the distal end to the proximal part, and its radioactivity assayed by liquid scintillation counting. In such conditions, a strong abrasion should result in a significant diminution of the activity of the hair segments which were in contact with the rotating cylinder, i.e., from 4 cm to 11 cm from the hair distal end.

The composition of the hair care composition of this invention and of a commercially available hair care composition used in this test are is set forth in the following TABLE 2.

TABLE 2

| Composition | Invention Composition Containing 0.1% 9/1 Ratio w/v | Commercial Composition Containing 0.1% 3/7 Ratio w/v |
|---|---|---|
| Absolute Ethyl alcohol | 35.00 v/v | 35.00 v/v |
| Antifungal agent | 0.02 | 0.02 |
| Perfume | 0.100 | 0.100 |
| Non-ionic emulsifier | 0.075 | 0.075 |
| d-Panthenyl ethyl ether | 0.09 | 0.03 |
| d-Panthenol | 0.01 | 0.07 |
| Lactic acid q.s. pH | 5.5 | 5.5 |
| Colorant | 0.00097 | 0.00097 |
| Deionised water q.s. | 100.00 ml | 100.00 ml |

The average results obtained after the abrasion during 30 minutes of hair treated with the hair care composition of this invention and the untreated hair clearly reveal a significant diminution of activity between segment no. 2 and segment no. 7 as compared to the non-abraded hair. This decrease of the radioactivity has been caused by the removal of radiolabelled cuticle scales and other hair debris during the abrasion, and represents the extent of damage induced by the continuous friction between the hair.

In such conditions, it is possible to define an Abrasion Index (AI) as the ratio of the quantity of keratin lost during the abrasion to the quantity of keratin which would have been removed if the abrasion would have been total.

Paired comparisons of the Abrasion Indices obtained on treated hair and untreated hair indicate a significant (p=0.052) reduction of abrasion of the samples treated with the hair care composition of this invention. This is clearly reflected in the average Abrasion Indices, calculated for the un-treated hair (AI=18.4±5.10) and the treated hairs (AI=9.7±3.03).

Similar tests carried out on hair samples treated with the commercial hair care composition revealed an increase of the abrasion after treatment with the commercial composition as compared to untreated hair. The average Abrasion Index calculated for 16 experiments confirms this observation, with AI=13.1±1.95 for commercial composition treated hair, and AI=8.6±2.78 for the un-treated hair.

Thus, whereas the commercially available hair care composition induced an increase in hair abrasion, the hair care composition of this invention decreased hair abrasion.

We claim:

1. In a hair care composition for the treatment of hair the improvement comprising employing in said composition 9 parts by weight d-panthenyl ethyl ether per 1 part by weight d-panthenol for a combined weight of from about 0.05% to about 1.0%, based on the weight of the composition.

2. A hair care composition of claim 1 wherein there is present in said composition from about 0.05% by weight to about 1.0% by weight of a mixture consisting of 9 parts d-panthenyl ethyl ether and 1 part d-panthenol.

3. A hair care composition of claim 2 wherein the mixture is present in the composition at about 0.1% to 0.5% by weight.

4. A hair care composition of claim 2 comprising about

| Components | w/v |
| --- | --- |
| Absolute Ethyl alcohol | 35.00 v/v |
| Antibacterial agent | 0.050 |
| Perfume | 0.100 |
| Non-ionic Emulsifier | 0.075 |
| d-Panthenyl ethyl ether | 0.09 |
| d-Panthenol | 0.01 |
| Ultraviolet filter agent | 0.025 |
| Colorant | 0.00062 |
| Lactic acid q.s. pH | 5.5 |
| Deionised water q.s. | 100 ml. |

5. A hair care composition of claim 2 comprising about

| Composition | w/w |
| --- | --- |
| Absolute Ethyl alcohol | 35.00 v/v |
| Antifungal agent | 0.02 |
| Perfume | 0.100 |
| Non-ionic emulsifier | 0.075 |
| d-Panthenyl ethyl ether | 0.09 |
| d-Panthenol | 0.01 |
| Lactic acid q.s. pH | 5.5 |
| Colorant | 0.00097 |
| Deionised water q.s. | 100.00 ml. |

* * * * *